United States Patent [19]

Eto et al.

[11] Patent Number: 5,847,078
[45] Date of Patent: *Dec. 8, 1998

[54] POLYPEPTIDE CAPABLE OF DIFFERENTIATING AND MATURING MALIGNANT CELLS INTO NORMAL CELLS OR CAPABLE OF ACCELERATING THE FORMULATION OF ERYTHROBLASTS

[76] Inventors: Yuzuru Eto, No. 2-7-11-303, Nakahara, Isogo-ku, Yokohama-shi, Kanagawa-ken; Tomoko Tsuji, No. 958, Kashimada, Saiwai-ku, Kawasaki-shi, Kanagawa-ken; Satoshi Takano, No. 11-16, Kamino-cho, Totsuka-ku, Yokohama-shi, Kanagawa-ken; Misako Takezawa, No. 7317-16, Izumi-cho, Totsuka-ku, Yokohama-shi, Kangawa-ken; Yasunori Yokogawa, No. 8-13-2, Fukuda, Yamato-shi, Kanagawa-ken; Hiroshiro Shibai, No. 14-15, Wakamatsu-cho, Chigasaki-shi, Kanagawa-ken, all of Japan

[ * ] Notice: The term of this patent shall not extend beyond the expiration date of Pat. No. 5,206,160 and Pat. No. 5,200,395.

[21] Appl. No.: 400,194

[22] Filed: Mar. 3, 1995

Related U.S. Application Data

[63] Continuation of Ser. No. 209,364, Mar. 14, 1994, abandoned, which is a continuation of Ser. No. 86,459, Jul. 6, 1993, abandoned, which is a continuation of Ser. No. 863,141, Apr. 2, 1992, abandoned, which is a continuation of Ser. No. 489,880, Mar. 7, 1990, abandoned, which is a continuation of Ser. No. 315,824, Feb. 23, 1989, abandoned, which is a continuation of Ser. No. 881,348, Jul. 2, 1986, abandoned.

[30] Foreign Application Priority Data

| Jul. 3, 1985 | [JP] | Japan | 60-146315 |
| Aug. 2, 1985 | [JP] | Japan | 60-170839 |
| Sep. 6, 1985 | [JP] | Japan | 60-197276 |
| Dec. 18, 1985 | [JP] | Japan | 60-284563 |

[51] Int. Cl.$^6$ ..................... C07K 4/12
[52] U.S. Cl. ............ 530/350; 530/324; 530/399; 930/260; 930/DIG. 820; 930/DIG. 800
[58] Field of Search ............... 530/324, 350, 530/399; 930/260, DIG. 820, DIG. 800

[56] References Cited

U.S. PATENT DOCUMENTS

| 4,740,587 | 4/1988 | Ling et al. | 530/313 |
| 4,760,021 | 7/1988 | Mimura et al. | 435/68 |
| 4,798,885 | 1/1989 | Masson et al. | 530/350 |
| 4,973,577 | 11/1990 | Vale, Sr. et al. | 530/313 |

FOREIGN PATENT DOCUMENTS

| 8606076 | 10/1986 | WIPO. | |
| 8700528 | 1/1987 | WIPO | 530/324 |
| 0222491 | 5/1987 | WIPO. | |

OTHER PUBLICATIONS

The Merck Manual, 11th ed. (1966), pp. 77–97.
Nicola et al, Chem. Abs. 102(25), 216019k.
Nagata et al, Chem. Abs. 88(11), 72644C.
Kashiwamura et al, Chem. Abs. 109(25), 223616a.
Chem. Abs., vol. 104, 1986, 953 d.
Nature 321 pp. 724–125, 776–782 (1986).
Nature 318, pp. 659–663 (1986).
Biochem. Biophys. Res. commun. 135, pp. 957–964 (1986).
Chem. Abs. 88 (9)–60952 P.–Okabe et al, (1978), p. 268.
Chem. Abs. 94 (7) –45433a–Bergess et al, (1981), p. 422.
Chem. Abs. 96 (7)–50392g, (1982), p. 456.
Biological Abstracts, No. 77, 1984, No. 517, F. Eithan et al "Modulation of the Maturation of Human Leukemic Promyelocytes to Granulocytes er Macrophages".
Patent Abstracts of Japan, vol. 9, No. 145 (C–287) [1968] Jun. 20, 1985, Midori Juji K.K.
Chemical Abstracts, vol. 100, No. 21, May 21, 1984, p. 485 Abstract No. 172963r; L. Matera et al "Soluble Factor(s) Released by Concanavalin A Activated Lymph Node Lymphocytes Induce Proliferation and Maturation of Chronic Lymphocytic Leukemia . . . ".
Chemical Abstracts, No. 94, No. 17, Apr. 27, 1981, p. 230, Abstract No. 133806e; P.H. Koeffler et al; "Phorbol Ester Effect on Differentiation of Human Myeloid Leukemia Cell Lines Blocked at Different Stages of Maturation".
Chemical Abstracts, vol. 97, No. 19, Nov. 8, 1982, p. 543, Abstract No. 160941p, P. Ralph et al; "Induction of Antibody–Dependent and Nonspecific Tumor Killing in Human Monocytic Leukemia Cells by Nonlymphocyte Factors and Phorbol Ester".

*Primary Examiner*—Ponnathapura Achutamurthy
*Assistant Examiner*—T. D. Wessendorf
*Attorney, Agent, or Firm*—Oblon, Spivak, McClelland, Maier & Neustadt, P.C.

[57] ABSTRACT

A physiologically active polypeptide, BUF-3, having the ability to differentiate and maturate human leukemia cells into normal cells and of accelerating the formation of erythroblasts is disclosed. The polypeptide has a molecular weight of 16±1 Kd as determined by SDS-electrophoresis in the presence of 1% mercaptoethanol, or 25±1 Kd, as determined by SDS-electrophoresis in the absence of mercaptoethanol.

1 Claim, 3 Drawing Sheets

POLYPEPTIDE CAPABLE OF DIFFERENTIATING AND MATURING MALIGNANT CELLS INTO NORMAL CELLS OR CAPABLE OF ACCELERATING THE FORMULATION OF ERYTHROBLASTS

This application is a Continuation of application Ser. No. 08/209,364, filed on Mar. 14, 1994, now abandoned; which is a continuation of application Ser. No. 08/086,459 filed on Jul. 6, 1993, abandoned; which is a continuation of Ser. No. 07/863,141 filed on Apr. 2, 1992, abandoned; which is a continuation of Ser. No. 07/489,880 filed on Mar. 7, 1990, abandoned; which is a continuation of application Ser. No. 07/315,824 filed on Feb. 23, 1989, abandoned; which is a continuation of application Ser. No. 06/881,348 filed on Jul. 2, 1986, abandoned.

BACKGROUND OF THE INVENTION

1. Field of the Invention

This invention relates to a physiologically active polypeptide. More particularly, it relates to a polypeptide capable of differentiating and maturing malignant cells into normal cells, or capable of accelerating the formation of erythroblasts.

2. Discussion of the Background

Studies on differentiation inducing i.e., substances (substances capable of transforming malignant cells into normal cells) for use in the relief of various cancers are actively underway all over the world. It is known that mouse Friend leukemia cells and human mononuclear leukemia cells, when treated with some chemicals or physiological factors, are differentiated or maturated into macrophages, granulocyte-like cells or erythrocyte-like cells, losing the properties unique to malignant cells, such as proliferation and transplantation capacity.

As such chemicals factors there are known polar compounds such as DMSO, lipopolysaccharides, immunopotentiating substances, antibiotics such as bleomycin and actinomycin D, vitamins, phorbol esters such as TPA (12-0-tetradecanoylphorbol-13-acetate), alginase, proteins such as histone, and others. A typical example of the physiological factors is D factor, which is a glycoprotein having a molecular weight of 40,000 to 50,000 and produced by fetal mouse cells (M1 cells) (Cancer & Chemotherapy: 9, 105–114, 1982). It is also known that stimulation of human mononuclear leukocytes with a mitogen, such as concanavalin A, gives CSF (leukocytic inducing factor) and D factor (molecular weight: 25,000 and 40,000, respectively). The D factor thus produced is capable of differentiating human promyelocytic leukemia cells (HL-60) into macrophage-like cells. Similarly, it was reported that stimulation of human mononuclear leukocytes with a mitogen, such as a lipopolysaccharide, yields a factor capable of differentiating human myeloid leukemia cells and human mononuclear leukemia cells [Proceedings of 43th General Meeting of the Japanese Cancer Association; No.639, p 190 (1984), and Japanese Patent Kokai No.28934 (1985)]. However, no human-derived, differentiation inducing factor capable of differentiating well-known Friend leukemia cells has yet been reported.

Many kinds of medicines have been used for the relief of anemia depending upon its cause. Iron preparations are generally employed for iron-deficiency anemia, vitamin $B_{12}$ and folic acid for malignant anemia, and adrenocortical steroids, such as corticoids, for hemolytic anemia. Of these, steroid hormones are known to have powerful erythropoietic stimulating action and are thus regarded as being efficacious medicines. However, they suffer the problem of strong side effects. It is generally accepted that their administration over long periods often causes troubles.

Recently erythropoietin has received attention as a substance which is closely related to the formation of erythrocytes and effective in alleviating anemia. Produced in the kidney, erythropoietin is a glycoprotein found in the $\alpha$-globulin fraction and which has a molecular weight of 45,000. It is defined as a humoral regulating factor which acts upon hematopoietic stem cells to accelerate their differentiation into erythroid cells and the formation of erythroblasts. It is expected as to be a new medicine for the treatment of anemia. However, it is difficult to supply this substance in sufficient quantities because it is now extracted from human urine, where it is contained in very small amounts. Studies on producing it by genetic techniques are also under way, but to date remain unsuccessful because of the difficulties associated with the fact that it is a glycoprotein.

Thus the object of this invention is to find, by using various types of human cells, a new malignant-cell-differentiating factor and a new factor effective for the treatment of anemia, and to determine its chemical nature.

SUMMARY OF THE INVENTION

To solve the above-mentioned problems, we examined various types of human cells for the production of differentiating factors. As a result, we have found that culturing human leukemia cells in the presence of a specific differentiation inducing substance yields a new human differentiation inducing factor, BUF-3, capable of differentiating and maturating mouse leukemia cells into normal cells. We suceeded in isolating BUF-3 from the culture solution, purifying it and characterizing its chemical nature. We also demonstrated that BUF-3 thus obtained is effective in alleviating anemia. This invention was accomplished based on these findings.

DETAILED DESCRIPTION OF THE PREFERRED EMBODIMENTS

Figure 1:
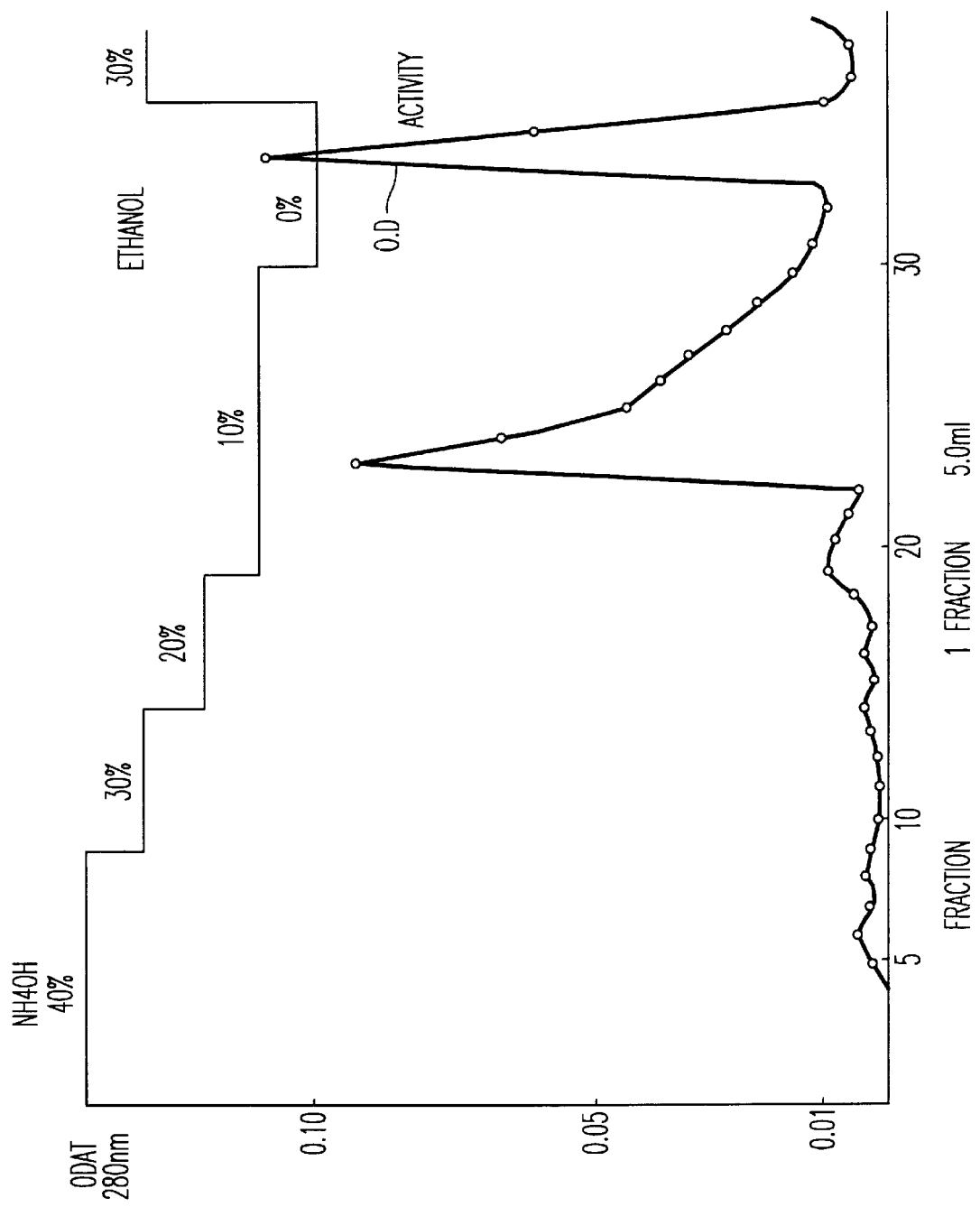
FIG. 1 is the hydrophobic chromatography elution pattern of the human differentiation inducing factor, BUF-3, of this invention on Butyl-Toyopearl.

The polypeptide of this invention, BUF-3, has the ability of differentiating and maturating human leukemia cells into normal cells (benign alteration) and of accelerating the formation of erythroblasts. Unlike substances of animal or microbial origin, this polypeptide, produced by human cells, has potential uses as a medicine for the treatment of human leukemia and anemia.

Human leukemia cells herein mean established strains derived from human leukemia, or myeloid cells which have been subjected to artificial malignant alteration. To be more specific, these include human histiocytic lymphoma cells [U-937 ATCC CRL 1593; Int. J. Cancer, 17, 565 (1976)]; human chronic myeloid leukemia cells [K562; Blood, 45, 321 (1975)]; human mononuclear leukemia cells [J-111; Blood, 10, 1010 (1955)]; and human acute mononuclear leukemia cells [THP-1; Int. J. Cancer, 26, 171–176 1980)]. The specific differentiation inducing substances are those substances which give BUF-3 upon contact with human leukemia cells. Illustrative examples include actinomycin D, Mitomycin C, concanavalin A and phorbol esters (TPA, etc.).

BUF-3 of this invention can be produced by culture of human leukemia cells in the presence of at least one of the specific differentiation inducing substances mentioned above. BUF-3 is accumulated in the culture solution (extracellular production).

Media commonly used for culturing animal cells may be employed for the culture of human leukemia cells in the method of this invention. A preferable example is Roswell Park Memorial Institute 1640 medium (hereinafter abbreviated as RPMI-1640 medium), but Dulbecco-modified Eagle's minimum essential medium and Click medium are also employed advantageously. Fetal bovine serum (hereinafter abbreviated as FBS), new-born bovine serum or horse serum is commonly added to these media. In this particular case, however, there is no need for such additives.

Human leukemia cells are cultured at 35 to 38° C. under a stream of 4 to 6% carbon dioxide gas by the static method or with gentle stirring, generally at a cell density of 1 to $5 \times 10^6$ cell/ml. The specific differentiation inducing substance may be added to the medium either initially or during the course of culture. The suitable amount to be added varies depending on its type; 0.1 to 10 μg/ml for actinomycin D and mitomycin C, and 1 to 500 ng/ml for TPA. BUF-3 is thus accumulated in the culture solution in one to five days.

The activity of BUF-3 can be measured according to a known technique [Proc. Natl. Acad. Sci., 71, 98 (1975)] using leukemia cells F5-5 induced by mouse Friend leukemia virus [Bibl. Haemat., 43, 37 (1976)]. Activity per ml of a sample solution is represented by reciprocal of the dilution rate of that sample solution at which differentiation of F5-5 cells is clearly noticed. When BUF-3 is produced by the method of this invention, resulting culture solutions generally show an activity of 4 to 1000 unit/ml.

BUF-3 can be purified according to the methods commonly used for proteins. For example, a culture solution is first concentrated by ultrafiltration, and proteins are isolated from the concentrate by salting out. This is followed by purification by dialysis and ion-exchange chromatography on an anionic exchanger. The crude protein preparation thus obtained is then freed from almost all the impurities contained by either hydrophobic chromatography or chromatofocusing. Higher degree of purification can be achieved if these two methods are combined. The product thus prepared can be further purified by reverse-phase high performance liquid chromatography, by high performance gel filtration using FPLC system (Fast Protein Peptide Polynucleotide Liquid Chromatography of Pharmacia Fine Chemicals) equipped with Superlose or mono QHR 5/5 column, or by ion-exchange chromatography.

BUF-3 thus purified has the following properties:
(1) Molecular weight
    16±1 Kd (SDS-electrophoresis in the presence of 1.0% mercaptoethanol
    25±1 Kd (SDS-electrophoresis in the absence of mercaptoethanol
(2) Isoelectric point
    pI 6.3±0.2 (chromatofocusing)
    pI 7.3 (electrofocusing)
(3) pH stability
    Stable within pH range betwen 2.0 and 10.0.
(4) Thermal stability
    Stable against heating at 65° C. for 60 minutes.
(5) Stability against organic solvents
    Stable against lower alcohols and acetonitrile.
(6) Resistance to protease
    Becomes completely deactivated by treatment with Pronase
(7) Specific activity
    $2 \times 10^6$ U/mg-protein
(8) Amino acid sequence at amino terminal Gly—Leu—Glu—X—Asp—Gly—Lys—Val—Asn—Ile—X—X—

Lys—Lys—Gln—Phe—Phe—Val—Ser—Phe—Lys—Asp—Ile—

Gly—Trp—Asn—Asp—Trp—Ile—Ile—Ala—Pro—Ser—Gly—Tyr (X: unidentified amino acid)
(9) Amino acid sequence of peptide fragment formed by cyanogen bromide
    Leu-Tyr-Tyr-Asp-Asp-Gly-Gln-Asn-Ile-Ile-Lys-Lys-Asp-Ile-Gln-Asn A polypeptide capable of differentiating and maturating malignant cells into normal cells and having the following properties:
(a) a molecular weight of 16±1 Kd as determined by SDS-electrophoresis in the presence of 1% mercaptoethanol, and of 25±1 Kd as determined by SDS-electrophoresis in the absence of mercaptoethanol;
(b) a peptide fragment, formed by cyanogen bromide cleavage of said polypeptide, having the following amino acid sequence:
    Leu-Tyr-Tyr-Asp-Asp-Gly-Gln-Asn-Ile-Ile-Lys-Lys-Asp-Ile-Gln-Asn
(c) said polypeptide being a homodimer, containing a disulfide bond, of the following amino acid sequence:

| | | | | | | | | | |
|---|---|---|---|---|---|---|---|---|---|
| 1 | | | | | | | | | 10 |
| Gly | Leu | Glu | Cys | Asp | Gly | Lys | Val | Asn | Ile |
| 11 | | | | | | | | | 20 |
| Cys | Cys | Lys | Lys | Gln | Phe | Phe | Val | Ser | Phe |
| 21 | | | | | | | | | 30 |
| Lys | Asp | Ile | Gly | Trp | Asn | Asp | Trp | Ile | Ile |
| 31 | | | | | | | | | 40 |
| Ala | Pro | Ser | Gly | Tyr | His | Ala | Asn | Tyr | Cys |
| 41 | | | | | | | | | 50 |
| Glu | Gly | Glu | Cys | Pro | Ser | His | Ile | Ala | Gly |
| 51 | | | | | | | | | 60 |
| Thr | Ser | Gly | Ser | Ser | Leu | Ser | Phe | His | Ser |
| 61 | | | | | | | | | 70 |
| Thr | Val | Ile | Asn | His | Tyr | Arg | Met | Arg | Gly |
| 71 | | | | | | | | | 80 |
| His | Ser | Pro | Phe | Ala | Asn | Leu | Lys | Ser | Cys |
| 81 | | | | | | | | | 90 |
| Cys | Val | Pro | Thr | Lys | Leu | Arg | Pro | Met | Ser |
| 91 | | | | | | | | | 100 |
| Met | Leu | Tyr | Tyr | Asp | Asp | Gly | Gln | Asn | Ile |
| 101 | | | | | | | | | 110 |
| Ile | Lys | Lys | Asp | Ile | Gln | Asn | Met | Ile | Val |
| 111 | | | | | | | | | |
| Glu | Glu | Cys | Gly | Cys | Ser. | | | | |

BUF-3 of this invention has activity to differentiate and maturate mouse Friend leukemia cells into normal cells and to accelerate the formation of erythroblasts.

Anemia in mice can be alleviated by administration of BUF-3. If leukemia cells induced by mouse Friend virus are transplanted into a mouse, its hematocrit value (volume percent of erythrocytes, which represents the severity of anemia more correctly than the number of erythrocytes) gradually decreases, with the result that the mouse becomes anemic one week after transplantation. In this case, if BUF-3 is intravenously injected immediately after transplantation, little drop is observed in hematocrit value and a significant difference is noticed after three weeks. If BUF-3 is administered to a mouse suffering from anemia one week after transplantation, the decline in hematocrit value is suppressed and the value begins to increase again two or three days later, clearly showing therapeutic effect of BUF-3 against anemia.

The medicine for the treatment of anemia of this invention is effective in preventing and curing human anemia caused by lowered erythrocyte productivity, with no toxicity against human cells. It is principally administered parenterally (intramuscularly, subcutaneously or intravenously). The suitable dose of effective ingredient (BUF-3) may vary with the condition of patients, but generally an amount within the range of 0.05 to 25 mg should be administered in several portions for adults. Hence, the suitable daily dose is in the range of 0.1 to 50 mg. The optimum dose is dependent upon the severity of anemia, weight of the patient and other factors regarded as important by those skilled in the art.

BUF-3 is primarily used as parenteral injections, but may also be employed in other dosage forms, such as capsules and tablets. Parenteral injections (e.g., subcutaneous, intramuscular and intravenous injections) may be prepared according to known techniques by addition of a pH regulator, buffering agent, stabilizer and preservative, as required. Oral preparations (e.g., tablets and capsules) may also be prepared by known methods by mixing with a binder, disintegrator and coloring agent).

EXAMPLE 1

Each of the human malignant leukemia cells listed in Table 1 was suspended in RPMI-1640 medium containing 5% FBS, or Dulbecco-modified Eagle's minimum essential medium containing 5% FBS, at a cell concentration of $1 \times 10^6$ cell/ml, and the suspensions thus obtained were placed in a flat-bottomed, 24-well microtiterplate (Pharcon) and incubated at 37° C. TPA was added to concentrations of 10 ng/ml and 100 ng/ml, the culture solution was taken out and centrifuged one, two, three, four and five days after the start of incubation, and each supernatant was measured for differentiation inducing activity against F5-5 cells. Cells cultured in the absence of TPA were used as control in this test. The result is summarized in Table 1.

TABLE 1

BUF-3 Production By Different Human Leukemia Cells

| Human Leukemia Cells | TPA Concn. (ng/ml) | Culture Period (day) | Activity (U/ml) |
| --- | --- | --- | --- |
| K-562 | 100 | 5 | 64 |
| U-937 | 100 | 5 | 16 |
| J-111 | 100 | 3 | 16 |
| HL-60 | 100 | 1 | 0 |
| THP-1 | 10 | 1 | 16 |
|  | 10 | 2 | 64 |
|  | 10 | 3 | 64 |

As can be seen from the table, the highest activity was observed with K-562 and THP-1 cells, followed by U-937 and J-111, but HL-60 cells showed no activity at all. A similar experiment was conducted to examine the effect of various differentiation inducing substances by using THP-1 cells. The result is summarized in Table 2.

TABLE 2

Effect of Differentiation Inducing Substances on BUF-3 Production by THP-1 Cells

| Differentiation Inducing Substance | Concn. | Culture Period (day) | Activity (U/ml) |
| --- | --- | --- | --- |
| Actinomycin D | 1 µg/ml | 3 | 0 |
|  | 5 µg/ml | 3 | 4 |
| Mitomycin C | 5 µg/ml | 3 | 0 |
|  | 10 µg/ml | 3 | 2 |
| ConA | 25 µg/ml | 3 | 8 |
| LPS* | 50 µg/ml | 3 | 0 |
| TPA | 100 ng/ml | 1 | 64 |
|  | 100 ng/ml | 2 | 64 |

*LPS derived from *E. coli*

EXAMPLE 2

Figure 2:
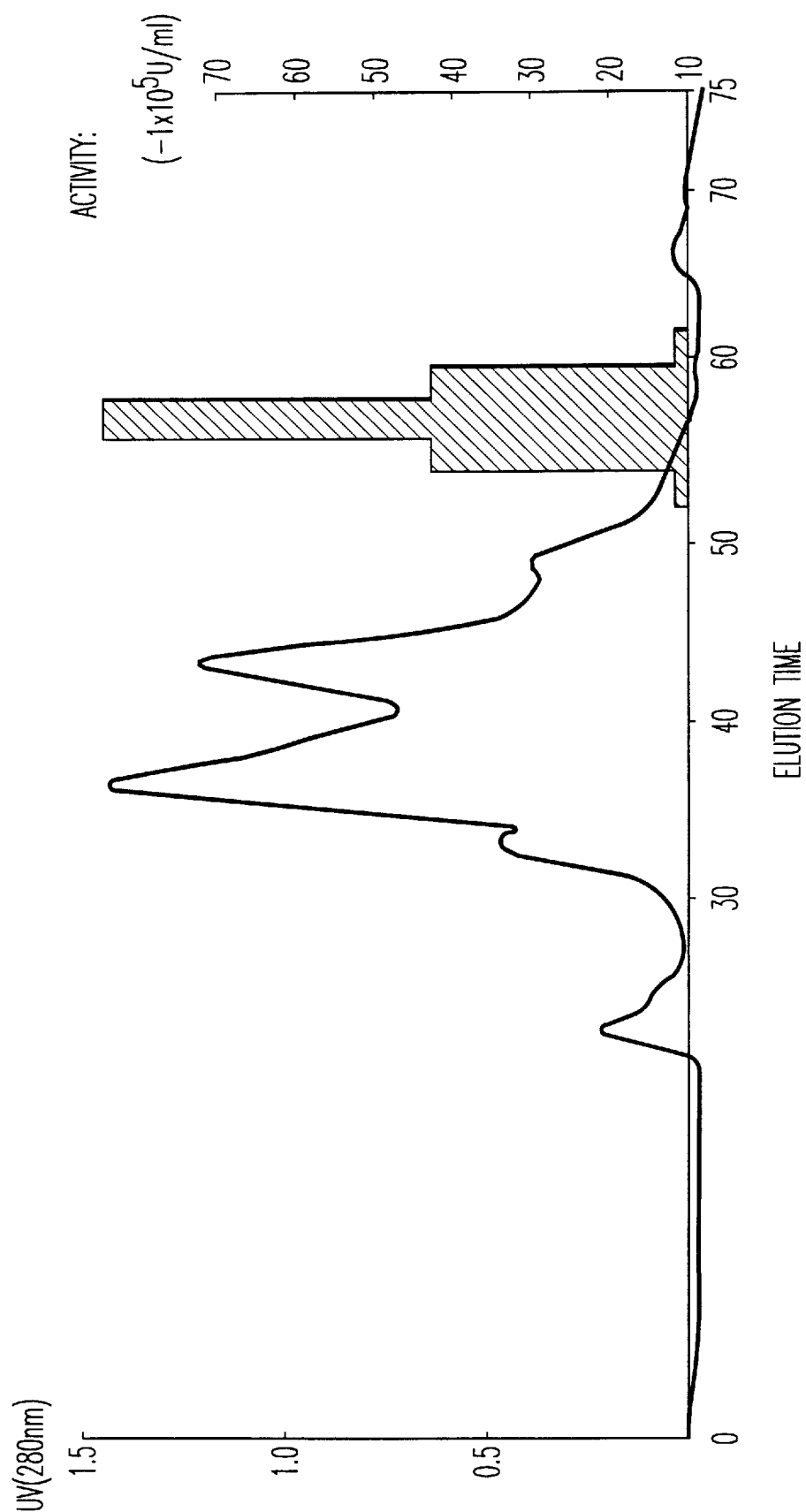
FIG. 2 is the gel filtration elution pattern of the human differentiation inducing factor, BUF-3, of this invention.
Figure 3:
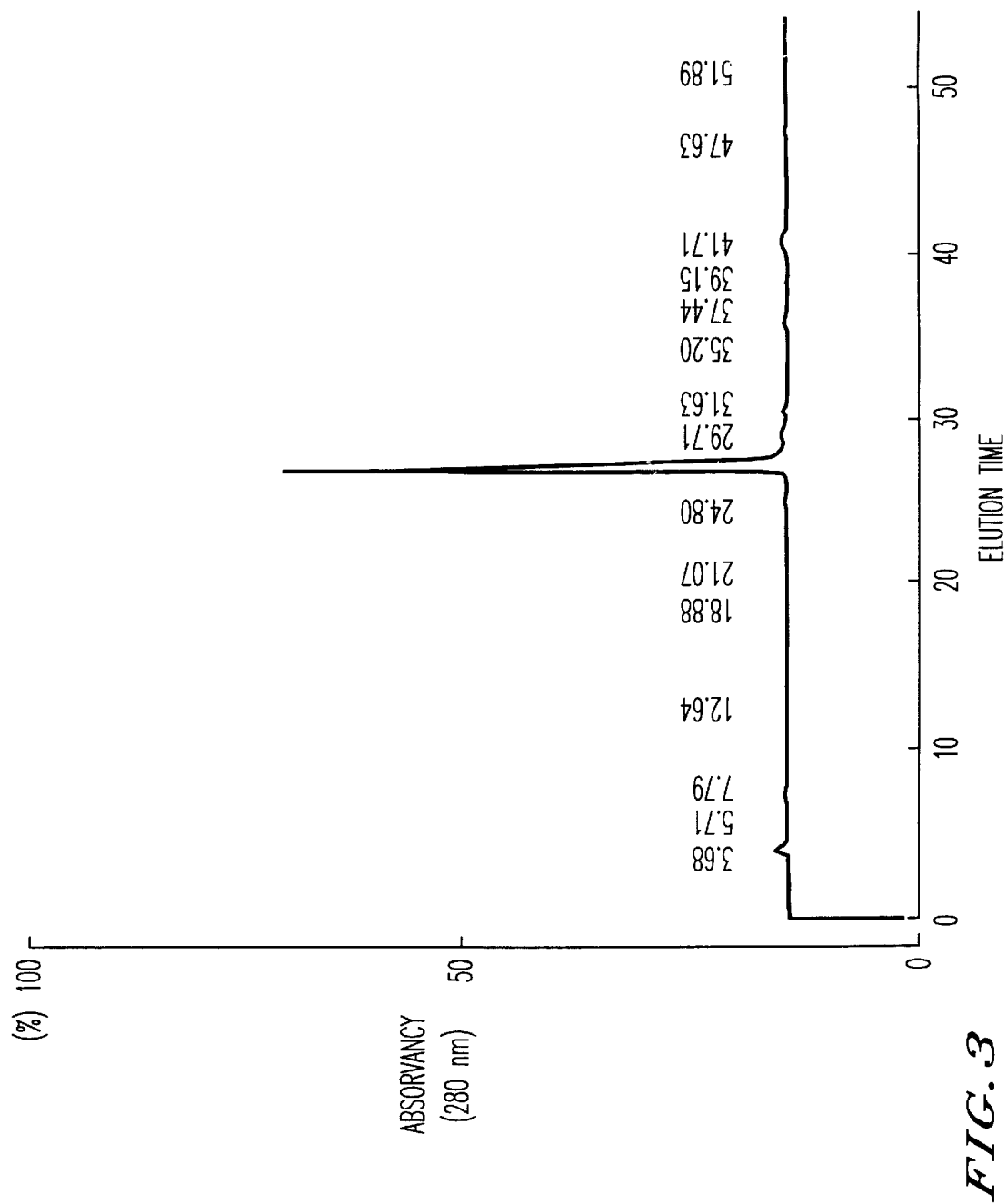
FIG. 3 is the reverse-phase high performance liquid chromatography elution pattern of the human differentiation inducing factor, BUF-3, of this invention.

A 20-liter Spinner flask was charged with 5.0 l of germ-free RPMI-1640 medium containing 5% fetal bovine serum, THP-1 cells obtained in the same way as in Example 1 were suspended in this medium at a density of $2 \times 10^5$ cell/ml, and cultured at 37° C. for four days. The culture solution was centrifuged. The THP-1 cells thus collected were transferred to 5.0 l of fresh RPMI-1640 medium containing no FBS, 10 ng/ml of TPA was added, and culture was continued at 37° C. for two hours with gentle stirring (at 100 rpm) to effect induction. Removal of the cells by centrifugation gave a culture solution with an activity of 20 U/ml. Ammonium sulfate was added to 70% saturation to 100 l of this culture solution, the precipitate which separated out was collected by centrifugation (10,000 rpm, 10 minutes) and dissolved in a small amount of 0.05M Tris-HCl buffer (pH: 7.8), and the aqueous solution was dialyzed against the same buffer as above. The dialyzate was loaded on DEAE-Toyopearl 650M column (7×70 cm) thoroughly equilibrated with the same 0.05M Tris-HCl buffer. After the column was washed with 5.0 l of the same buffer, the adsorbed portion was eluted with 0.05M Tris-HCl buffer solutions containing 0 to 0.2M sodium chloride. The active substance could be eluted by 0.1M sodium chloride solution. This active fraction was collected, solid ammonium sulfate was added to 70% saturation, and the precipitate thus formed was collected by centrifugation and dissolved in 20 ml water. To this aqueous solution was added 20 ml of 80%-saturated ammonium sulfate solution, and the resulting mixture was loaded on Butyl-Toyopearl 650M column (25×30 cm) previously equilibrated with 0.05M Tris-HCl buffer pH:7.7). Stepwise reduction in the concentration of ammonium sulfate, followed by elution with 30 % ethanol, gave active fractions containing the differentiation inducing substance. FIG. 1 shows the elution pattern in t h e hydrophobic chromatography on Butyl-Toyopearl. The active fractions collected were concentrated under reduced pressure to remove ethanol, the concentrate was dialyzed against 0.05M Tris-HCl buffer (pH: 7.7), and the dialyzate was subjected to gel filtration through Superlose (Pharmacia's gel filtration column). The gel-filtration elution pattern is shown in FIG. 2. As may be seen from the figure, the elution time of the active substance against F5-5 is 56.0 minutes, from which the molecular weight of BUF-3 may be calculated by comparison with that of a standard protein, giving a value of 10±0.5 Kd. This sample was dialyzed against 0.05M Tris-HCl buffer (pH: 8.0) and further purified by the Pharmacia FPLC (Fast Protein Peptide Polynucleotide Liquid Chromatography) system using Mono QHR 5/5 column (Pharmacia's anion exchanger) equilibrated with the same buffer as above. Gradient elution was conducted using sodium chloride solutions of 0.05M to 0.1M concentrations, and the active fraction was obtained at a salt concentration of about 0.1M. The purification factor of this step was approximately 5, giving nearly a single protein. It was then subjected to reverse-phase high performance liquid chromatophy using HIPORE RP304 (C-4 reverse-phase column; Bio-rad Laboratories); 0.1% trifluoroacetic acid was used as developing solution, and elution was carried out with the concentration of n-propanol linearly increased from 0% to 80%. The elution pattern is shown in FIG. 3. In this figure, the protein peak was in precise agreement with activity peak. 100 μg of pure sample was obtained from this active fraction. This sample was subjected to SDS-polyacrylamide gel electrophoresis (gel concentration: 15.0%, in the presence of 1.0% mercaptoethanol), giving a single protein band at 16 Kd (silver staining method), with no other protein band at all. A value of 25 Kd was obtained when measured in the absence of mercaptoethanol. The specific activity of the pure sample thus otained was about $2\times10^6$ U/mg.

This purified sample (10 μg) was subjected to the Edman degradation using a gas-phase amino acid sequencing analyzer (Model 470A; Applied Biosystem), with the phenylthiohydantoin amino acids successively liberated being analyzed by high performance liquid chromatography (HPLC Model SP8100 of Spectrophysics Co.; column: Solvax ODS of DuPont). As a result, the amino acid sequence at amino terminal of BUF-3 was found to be as shown below.

Gly-Leu-Glu-X-Asp-Gly-Lys-Val-Asn-Ile-X-X-Lys-Lys-Gln-Phe-Phe-Val-Ser-Phe-Lys-Asp-Ile-Gly-Trp-Asn-Asp-Trp-Ile-Ile-Ala-Pro-Ser-Gly-Tyr (X in the above formula is an amino acid residue that could not be analyzed by the gas-phase amino acid analyzer.)

This sample (100 μg) was dissolved in 70% formic acid, a small amount of cyanogen bromide was added, and the cyanogen bromide cleavage was effected at room temperature for 24 hours. At the end of reaction, the resulting peptide fragment was isolated by high performance liquid chromatography (Shimadzu's HPLC Model LC-4A; column: Beckmann's ALTEX ULTRA PORE TM RPSC; gradient elution with eluent altered from 0.1% trifluoroacetic acid to 80% acetonitrile), and its amino acid sequence was determined by using the same amino acid sequencing analyzer as above. The result is:

Leu-Tyr-Tyr-Asp-Asp-Gly-Gln-Asn-Ile-Ile-Lys-Lys-Asp-Ile-Gln-Asn

Isoelectric point, pH stability and other properties of this sample were:
(1) Isoelectric point
   pI 6.3±0.2 (chromatofocusing)
   pI 7.3±0.2 (electrofocusing)
(2) pH stability
   Stable within pH range between 2.0 and 10.0 (at 4° C. for 7 hours).
(3) Thermal stability
   Stable against heating at 65° C. for 60 minutes (at pH 7.4).
(4) Stability against organic solvents
   Stable against lower alcohols and acetonitrile (at 25° C.).
(5) Resistance to protease
   Becomes completely deactivated by treatment with Pronase (a prescribed amount of BUF-3 was dissolved in 1% $NaHCO_3$ solution, Pronase was added in an amount 1/10 that of BUF-3, and the mixture was allowed to stand overnight at 37° C.).

Isoelectric point by chromatofocusing was measured according to the procedure given below. A purified sample was dialyzed against 25mM bis-Tris-HCl buffer (pH: 7.0), the dialyzate was loaded on a Polybuffer Exchanger PBE94 column (1.0×40 cm; Pharmacia Fine Chemicals), and the adsorbed portion was eluted with 1:10 dilution of Polybuffer (pH: 5.0). Isoelectric point was represented by the pH at which active fractions were eluted.

Isoelectric point by electrofocusing was measured by using an electrofocusing apparatus (LKB-Multiphore) and a reagent therefor (Ampholine), both products of LKB Inc. of Sweden, according to the LKB-Ampholine PAG plate method. A sample was settled on a plate gel (LKB1804-101, pH: 3.5–9.5), electrophoresis was continued for 2.5 hours at an impressed voltage of 1500 volts, and isoelectric point was determined by using, as marker, Pharmacia's isoelectric point measurement kit (pH: 3 to 10). The result was an isoelectric point of 7.3. The same value was also obtained in the presence β-mercaptoethanol.

The THP-1 cells used in this invention had been supplied by the authors of Int. J. Cancer, 26, 171–176 (1980). THP-1 cells are also described in Proc. Natl. Acad. Sci.: U.S.A.80, 5397–5401 (1983) and in Cancer, Research, 42, 484–489 (1982), and samples were supplied to these research organizations too. We are ready to supply THP-1 cells to any authorized research institute upon request.

EXAMPLE 3

An animal test was conducted using ddy mice (male, 5-week age; Tokyo Experimental Animal Co. Ltd.), with each group consisting of five animals. Mouse Friend leukemia cells, F5-5, serially subcultured in mouse ascites, were transplanted into the abdomen of each test animal ($2\times10^6$ cells for each). BUF-3 (freeze-dried sample) was dissolved in sterile physiological saline, giving a parenteral injection of 5000 U/ml, and this preparation was abdominally or intravenously injected to the members of the test group for consecutive three days from the next day after transplantation (0.2ml=1000 U for each). Blood samples were collected from the caudal vein 14 days and 21 days after transplantation of F5-5 cells, and the hematocrit values were measured in a usual way after centrifugation at 12,000 rpm for 5 minutes. Physiological saline was injected to the control group in place of BUF-3. The result is summarized in Table 3.

TABLE 3

| | Hematocrit Values | | | |
|---|---|---|---|---|
| | Before transplantation | After 14 days | After 21 days | |
| Control group Test group: | 44.3 ± 2.3 | 29.7 ± 11.9 | 28.8 ± 2.9 | *** |
| Intravenous | 44.6 ± 3.2 | 39.0 ± 15.2 | 41.9 ± 12.2 | * |
| Abdominal | 45.1 ± 1.3 | 41.9 ± 6.3 | 39 ± 9.0 | ** |

(*.*) (.): Significant difference at 95% probability

Separately, 0.2 ml of the BUF-3 parenteral preparation was intravenously injected to another group of mice 14 days after transplantation of F5-5 cells, and the hematocrit values were measured after 21 days. The result was 35±8.0, clearly indicating an increase in hematocrit value in the test group.

Normal mice, intravenously injected with 50 μg (2.5 mg/Kg) of BUF-3, were grown for two months to investigate its toxicity. All the mice grew normally, with no abnormality observed at all.

Effects Achieved By The Invention

The medicine for the treatment of anemia of this invention is effective in preventing and curing anemia caused by Friend leukemia, and hence can be used for the relief of anemia due to a deficiency of erythrocytes and hemoglobin caused by malignant tumors such as leukemia, multiple myeloma, or lymphoma.

What is claimed is:

1. A polypeptide having the following characteristics,
   (1) Molecular weight
      16±1 Kd (SDS-electrophoresis in the presence of 1.0% mercaptoethanol)
      25±1 Kd (SDS-electrophoresis in the absence of mercaptuethanol
   (2) Isoelectric point
      pI 6.3±0.2 (chromatofocusing)
      pI 7.3 (electrofocusing)
   (3) pH stability
      Stable within pH range between 2.0 and 10.0
   (4) Thermal stability
   (4) Thermal stability
      Stable against heating at 65° C. for 60 minutes
   (5) Stability against organic solvents
      Stable against lower alcohols and acetonitrile
   (6) Resistance to protease
      Becomes completely deactivated by treatment with Pronase
   (7) Amino acid sequence at amino terminal Gly—Leu—Glu—X—Asp—Gly—Lys—Val—Asn—Ile—X—X—
   Lys—Lys—Gln—Phe—Phe—Val—Ser—Phe—Lys—Asp—Ile—
   Gly—Trp—Asn—Asp—Trp—Ile—Ile—Ala—Pro—Ser—Gly—Tyr (wherein X is a naturally occurring amino acid)
   (8) Amino acid sequence of peptide fragment formed by cyanogen bromide
      Leu-Tyr-Tyr-Asp-Asp-Gly-Gln-Asn-Ile-Ile-Lys-Lys-Asp-Ile-Gln-Asn
      and wherein said polypeptide is expressed when human malignant leukemia cells selected from the group consisting of K-562, THP-1 and J-111 are cultured in a medium to which 12-0-tetradecanoylphorbol-13-acetate is added.

* * * * *

UNITED STATES PATENT AND TRADEMARK OFFICE
CERTIFICATE OF CORRECTION

PATENT NO. : 5,847,078
DATED : December 8, 1998
INVENTOR(S) : Yuzuru ETO et al.

It is certified that error appears in the above-identified patent and that said Letters Patent is hereby corrected as shown below:

On the title page, item [73] Assignee should be:

-- [73] Assignee: Ajinomoto Co., Inc., Tokyo, Japan--

Signed and Sealed this

Seventeenth Day of August, 1999

Attest:

Q. TODD DICKINSON

Attesting Officer

Acting Commissioner of Patents and Trademarks